(12) United States Patent
Mizuno et al.

(10) Patent No.: US 9,157,911 B2
(45) Date of Patent: Oct. 13, 2015

(54) ASSAY METHOD USING MAGNETIC SILICA PARTICLES AND REAGENT FOR SAID ASSAY METHOD

(75) Inventors: Yusuke Mizuno, Kyoto (JP);
Masamitsu Miyamori, Kyoto (JP);
Shinjiro Matsuda, Hyogo (JP); Yo Yagura, Hyogo (JP)

(73) Assignees: SANYO CHEMICAL INDUSTRIES, LTD., Kyoto (JP); WAKO PURE CHEMICAL INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/123,299

(22) PCT Filed: May 31, 2012

(86) PCT No.: PCT/JP2012/064219
§ 371 (c)(1),
(2), (4) Date: Jan. 30, 2014

(87) PCT Pub. No.: WO2012/173002
PCT Pub. Date: Dec. 20, 2012

(65) Prior Publication Data
US 2014/0154713 A1    Jun. 5, 2014

(30) Foreign Application Priority Data
Jun. 15, 2011 (JP) .................. 2011-133104

(51) Int. Cl.
| | | |
|---|---|---|
| G01N 33/53 | (2006.01) | |
| G01N 33/543 | (2006.01) | |
| G01N 33/552 | (2006.01) | |
| G01N 33/553 | (2006.01) | |
| C01B 33/18 | (2006.01) | |
| B82Y 30/00 | (2011.01) | |

(52) U.S. Cl.
CPC .......... *G01N 33/54326* (2013.01); *B82Y 30/00* (2013.01); *C01B 33/18* (2013.01); *G01N 33/5434* (2013.01); *G01N 33/552* (2013.01); *G01N 33/553* (2013.01); *C01P 2004/64* (2013.01); *C01P 2006/42* (2013.01)

(58) Field of Classification Search
None
See application file for complete search history.

(56) References Cited

U.S. PATENT DOCUMENTS

| | | | |
|---|---|---|---|
| 4,554,088 | A | 11/1985 | Whitehead et al. |
| 4,672,040 | A | 6/1987 | Josephson |
| 6,562,209 | B1 | 5/2003 | Sullivan et al. |
| 2009/0017518 | A1 | 1/2009 | Wu et al. |

FOREIGN PATENT DOCUMENTS

| | | |
|---|---|---|
| CN | 1952113 | 4/2007 |
| CN | 101013620 | 8/2007 |
| CN | 101256864 | 9/2008 |
| CN | 101306841 | 11/2008 |
| CN | 101345113 | 1/2009 |
| CN | 101865919 | 10/2010 |
| EP | 0 420 053 | 4/1991 |
| ES | 2 208 121 | 6/2004 |
| JP | 60-1564 | 1/1985 |
| JP | 3-120467 | 5/1991 |
| JP | 4-168360 | 6/1992 |
| JP | 8-9995 | 1/1996 |
| JP | 2000-40608 | 2/2000 |
| JP | 2000-256388 | 9/2000 |
| JP | 2008-116265 | 5/2008 |
| JP | 2010-32283 | 2/2010 |
| KR | 2009-0088299 | 8/2009 |
| WO | 2004/051278 | 6/2004 |

OTHER PUBLICATIONS

Qu et al. (Microporous and Mesoporous Materials 2009 vol. 117, p. 402-405).*
Bumb et al. Nanotechnology 2008 vol. 19, p. 1-6.*
Santra et al. Langmuir 2001 vol. 17, p. 2900-2906.*
Sun et al. JACS 2002 vol. 124, p. 8204-8205.*
International Search Report issued Aug. 7, 2012 in International (PCT) Application No. PCT/JP2012/064219.
Smith et al., "Optimization of antibody-conjugated magnetic nanoparticles for target preconcentration and immunoassays", Analytical Biochemistry, vol. 410, Nov. 13, 2010, pp. 124-132.
Dittmer et al., "Sensitive and rapid immunoassay for parathyroid hormone using magnetic particle labels and magnetic actuation", Journal of Immunological Methods, vol. 338, Jul. 25, 2008, pp. 40-46.
Mahmoudi et al., "Superparamagnetic iron oxide nanopartides (SPIONs): Development, surface modification and applications in chemotherapy", Advanced Drug Delivery Reviews, vol. 63, May 26, 2010, pp. 24-46.

* cited by examiner

*Primary Examiner* — Jacob Cheu
(74) *Attorney, Agent, or Firm* — Wenderoth, Lind & Ponack, L.L.P.

(57) ABSTRACT

In the method of assaying an analyte in a sample of the present invention, magnetic silica particles are used. The magnetic silica particles include: silica particles containing 60 to 95% by weight of a superparamagnetic metal oxide that has an average particle size of 1 to 15 nm; and the analyte, an analog of the analyte, or a substance capable of specifically binding to the analyte immobilized on the surface of the silica particles.

45 Claims, No Drawings

ASSAY METHOD USING MAGNETIC SILICA PARTICLES AND REAGENT FOR SAID ASSAY METHOD

TECHNICAL FIELD

The present invention relates to a method of assaying an analyte using magnetic silica particles, and a reagent for the assay method. The present invention specifically relates to an assay method and a reagent for the support of diagnosis, the support of checking therapeutic effects, and the confirmation of the degree of purification in protein purification and cell separation, for example.

BACKGROUND ART

Conventional methods of assaying or purifying biological materials in samples, such as proteins in biological samples, exemplarily include a method in which proteins in a biological sample are captured on the surface of particles to which the proteins can bind, the particles are washed so that impurities excluding the target proteins in the biological sample are removed and the particles capturing the proteins are collected, and the amount of the proteins bound to the particles is calculated. The conventional methods also include a method in which particles capturing the protein are mixed in a protein-dissociating solution in order to dissociate the protein from the particles, and the proteins are purified by dissociating the proteins in the protein-dissociating solution.

In the above assay methods, magnetic particles are used because such magnetic particles are easily isolated and collected by the magnetic force. For example, Patent Literature 1 discloses magnetic silica particles including core particles of iron oxide and silica coating on the surface of the core particles. However, the magnetic substance of such magnetic particles is a ferromagnetic substance. This ferromagnetism causes the magnetic substance itself to form a temporary magnetic field even after removal of the magnetic field applied upon collection, leading to self-association of the particles. This results in poor washability and/or adverse effects on the subsequent operations (e.g. immune response).

For the purpose of preventing the self-association of a magnetic substance due to the ferromagnetism, Patent Literature 2 discloses magnetic silica particles with a superparamagnetic substance. If such magnetic particles have a small particle size, the particles contain a small amount of the magnetic substance and require a long time to be collected by the magnetic force. If the magnetic particles have a large particle size, the particles have a small specific surface area and can capture only a small amount of protein.

CITATION LIST

Patent Literature

Patent Literature 1: JP 2000-256388 A
Patent Literature 2: JP 2000-40608 A

SUMMARY OF INVENTION

Technical Problem

The present invention aims to provide a method of assaying an analyte using magnetic silica particles which have excellent bindability in carrying the analyte, an analog of the analyte, or a substance capable of specifically binding to the analyte, have excellent collectability by the magnetic force and dispersibility in the absence of the magnetic force, and can show excellent sensitivity in immunoassay even after short-time washing; and to provide a reagent for such an assay method.

Solution to Problem

The present inventors have performed eager studies for achieving the above objects, and have arrived at the present invention. The present invention relates to a method of assaying an analyte in a sample in which magnetic silica particles are used, the magnetic silica particles including: silica particles containing 60 to 95% by weight of a superparamagnetic metal oxide that has an average particle size of 1 to 15 nm; and the analyte, an analog of the analyte, or a substance capable of specifically binding to the analyte immobilized on a surface of the silica particles. The present invention also relates to a reagent for the assay method, including magnetic silica particles that include: silica particles containing 60 to 95% by weight of a superparamagnetic metal oxide that has an average particle size of 1 to 15 nm; and an analyte, an analog of the analyte, or a substance capable of specifically binding to the analyte immobilized on the surface of the silica particles.

Advantageous Effects of Invention

The assay method and the reagent of the present invention enable easy B/F separation by magnetically collecting magnetic silica particles. Since the magnetic silica particles contain a superparamagnetic metal oxide, their magnetic characteristics provide excellent redispersibility of the particles after magnetic collection. This enables a short-time assay (detection) of an analyte at high sensitivity.

DESCRIPTION OF EMBODIMENTS

The present invention can be applied to any analytes usually used in assays in this field. Typical examples of analytes include proteins, lipoproteins, nucleic acids, immunoglobulins, blood coagulation-relating factors, antibodies, enzymes, hormones, tumor markers, cardiac markers, and drugs in samples of biological origin such as biological fluids (e.g. serum, blood, plasma, and urine), lymph, hemocytes, and cells. Specific examples thereof include proteins such as albumin, hemoglobin, myoglobin, transferrin, protein A, and C-reactive protein (CRP); lipoproteins such as high-density lipoproteins (HDL), low-density lipoproteins (LDL), and very-low-density lipoproteins; nucleic acids such as deoxyribonucleic acid (DNA) and ribonucleic acid (RNA); enzymes such as alkaline phosphatase, amylase, acid phosphatase, γ-glutamyltransferase (γ-GTP), lipase, creatine kinase (CK), lactate dehydrogenase (LDH), glutamic oxaloacetic transaminase (GOT), glutamic pyruvic transaminase (GPT), renin, protein kinase (PK), and tyrosine kinase; immunoglobulins such as IgG, IgM, IgA, IgD, and IgE (and fragments thereof such as Fc fragment, Fab fragment, and F(ab)$_2$ fragment); blood coagulation-relating factors such as fibrinogen, fibrin degradation products (FDP), prothrombin, and thrombin; antibodies such as anti-streptolysin O antibody, anti-Hepatitis B surface antigen (HBs antigen) antibody, anti-Hepatitis C antibody, and anti-rheumatoid factor; hormones such as thyroid-stimulating hormones (TSH), thyroid hormones (FT3, FT4, T3, T4), parathyroid hormones (PTH), human chorionic gonadotropin (hCG), and estradiol (E2); tumor markers such as α-fetoprotein (AFP), carcinoembryonic antigen (CEA), CA19-9, and prostate specific antigen (PSA); cardiac markers such as troponin T (TnT), N-terminal fragment of brain natriuretic peptide precursor (NT-proBNP); and drugs such as anticonvulsants, antibiotics, and theophylline. Preferable among the above substances are antibodies, hormones, tumor markers, and cardiac markers.

The analog of an analyte in the present invention may be any substance which is competitive with the analyte when the analog exists during a reaction between the analyte and the analyte-binding substance. For example, the analog may be any substance which is bindable to an analyte-binding site of a substance capable of specifically binding to the analyte ("analyte-binding substance"). That is, the analog may also be any substance having the same binding site as that of the analyte which is bindable to the analyte-binding substance.

The substance capable of specifically binding to an analyte (analyte-binding substance) in the present invention may be a substance binding to the analyte or its analog owing to an interaction such as "antigen"-"antibody" interaction, "glycan"-"protein" interaction, "glycan"-"lectin" interaction, "enzyme"-"inhibitor" interaction, "protein"-"peptide chain" interaction, "chromosome or nucleotide chain"-"nucleotide chain" interaction, or "nucleotide chain"-"protein" interaction. In each of the interactions, one is an analyte or its analog and the other is an analyte-binding substance. For example, in the case where the analyte or its analog is an "antigen", the analyte-binding substance is an "antibody". In the case where the analyte or its analog is an "antibody", the analyte-binding substance is an "antigen" (the same shall apply to the other interactions).

Specific examples of the substance include nucleotide chains (e.g. oligonucleotide chain and polynucleotide chain); chromosomes; peptide chains (e.g. C-peptide and angiotensin I); proteins (e.g. serum proteins such as procalcitonin, immunoglobulin A (IgA), immunoglobulin E (IgE), immunoglobulin G (IgG), immunoglobulin M (IgM), immunoglobulin D (IgD), β-microglobulin, albumin, degradation products thereof, and ferritin); enzymes (e.g. amylases (e.g. pancreas-type, salivary-type, and X-type amylases), alkaline phosphatases (e.g. liver-type, bone-type, placental-type, and small-intestinal-type alkaline phosphatases), acid phosphatases (e.g. PAP), γ-glutamyltransferases (e.g. kidney-type, pancreas-type, and liver-type γ-glutamyltransferases), lipases (e.g. pancreas-type and stomach-type lipases), creatine kinases (e.g. CK-1, CK-2, and mCK), lactate dehydrogenases (e.g. LDH1 to LDH5), glutamic oxaloacetic transaminases (e.g. ASTm and ASTs), glutamic pyruvic transaminases (e.g. ALTm and ALTs), cholinesterases (e.g. ChE1 to ChE5), leucine aminopeptidases (e.g. C-LAP, AA, and CAP), renin, protein kinase, and tyrosine kinase), and inhibitors of these enzymes; hormones (e.g. PTH, TSH, insulin, LH, FSH, and prolactin), receptors (e.g. estrogen receptor and TSH receptor); ligands (e.g. estrogen and TSH); microorganisms such as bacteria (e.g. *Mycobacterium tuberculosis, Streptococcus pneumoniae, Corynebacterium diphtheriae, Neisseria meningitidis, Neisseria gonorrhoeae, Staphylococcus, Streptococcus*, enteric bacteria, *Escherichia coli*, and *Helicobacter pylori*), viruses (e.g. Rubella virus, herpesvirus, hepatitis virus, ATL virus, AIDS virus, influenza virus, adenovirus, enterovirus, poliovirus, EB virus, HAV, HBV, HCV, HIV, and HTLV), fungi (e.g. *Candida* and *Cryptococcus*), spirochaeta (e.g. *Leptospira* and *Treponema pallidum*), *Chlamydia*, and *Mycoplasma*; proteins, and peptides and carbohydrate antigens derived from these microorganisms; allergens causing allergies such as bronchial asthma, allergic rhinitis, and atopic dermatitis (e.g. house dust, mites and ticks such as *Dermatophagoides farina* and *Dermatophagoides pteronyssinus*, pollen of *Cryptomeria japonica, Chamaecyparis obtusa, Paspalum thunbergii, Ambrosia artemisiifolia* var. *elatior, Phleum pratense, Anthoxantum odoratum*, and *Secale cereale*, allergens derived from animals including cats, dogs, and crabs, food including rice and albumen, fungi, insects, wood, drugs, and chemicals); lipids (e.g. lipoproteins); proteases (e.g. trypsin, plasmin, and serine proteases); tumor marker protein antigens (e.g. PSA, PGI, and PGII); carbohydrate antigens (e.g. AFPs (e.g. L1 to L3), hCGs (hCG family), transferrin, IgG, thyroglobulin, Decay-accelerating-factor (DAF), carcinoembryonic antigens (e.g. CEA, NCA, NCA-2, and NFA), CA19-9, PIVKA-II, CA125, prostate specific antigen, tumor marker carbohydrate antigens having unique glycans produced by cancer cells, and ABO carbohydrate antigens); glycans (e.g. hyaluronic acid, β-glucan, and glycans in the carbohydrate antigens); glycan-binding proteins (e.g. hyaluronic acid-binding proteins and β-glucan-binding proteins); phospholipids (e.g. cardiolipin); lipopolysaccharides (e.g. endotoxin); chemicals (e.g. T3, T4, and endocrine disruptors such as tributyltin, nonylphenol, 4-octylphenol, di-n-butyl phthalate, dicyclohexyl phthalate, benzophenone, octachlorostyrene, and di-2-ethylhexyl phthalate); drugs administered to or inoculated into human bodies and metabolites thereof; aptamers; nucleic acid-binding substances; and antibodies against these. The antibodies used in the present invention also include degradation products such as Fab and $F(ab')_2$ fragments generated by proteolytic enzymes such as papain and pepsin, and by chemical decomposition.

The aforementioned analyte-binding substance is preferably a substance capable of binding to an analyte or its analog by "antigen"-"antibody" interaction or "glycan-protein" interaction. Specifically, the aforementioned analyte-binding substance is preferably an antibody against an analyte or its analog, an antigen to which an analyte or its analog binds, or a protein binding to an analyte or its analog, and more preferably an antibody against an analyte or its analog, or a protein binding to an analyte or its analog.

The magnetic silica particles in the present invention are prepared by dispersing a superparamagnetic metal oxide that has an average particle size of 1 to 15 nm in a silica matrix.

The average particle size of the superparamagnetic metal oxide in the present invention is an average value of the particle sizes of any 200 particles of superparamagnetic metal oxide measured using a scanning electron microscope.

The average particle size of the superparamagnetic metal oxide can be controlled by adjusting the metal ion concentration in production of the superparamagnetic metal oxide to be mentioned later. The average particle size of the superparamagnetic metal oxide may be set to a desired value by any usual method such as classification.

The term "superparamagnetic" herein means the following: that is, an external magnetic field applied to a substance induces a temporary magnetic field from the substance and causes an alignment of the respective atomic magnetic moments of the substance, whereas the magnetic field from the substance disappears and the partial alignment of the atomic magnetic moments is lost when the external magnetic field is removed.

Examples of the superparamagnetic metal oxide that shows superparamagnetism at an average particle size of 1 to 15 nm include oxides of iron, cobalt, nickel, and alloys thereof. Iron oxides are particularly preferred because iron oxides have excellent sensitivity to the magnetic field. Each of the superparamagnetic metal oxides may be used alone, or two or more of these may be used in combination.

It is difficult to synthesize a metal oxide with an average particle size of smaller than 1 nm. The metal oxide with an average particle size of greater than 15 nm causes the magnetic silica particles to have ferromagnetism. In this case, the magnetic substance itself forms a temporary magnetic field and the particles self-associate with each other even after the magnetic field is removed in practical use, resulting in poor washability and/or adverse effects on immune response.

The iron oxide may be selected from various known iron oxides. Preferable are magnetite, γ-hematite, an intermediate iron oxide between magnetite and α-hematite, and an intermediate iron oxide between γ-hematite and α-hematite because they have excellent chemical stability. Magnetite is more preferred because magnetite has a high saturation magnetization and has excellent sensitivity to an external magnetic field.

The amount of the superparamagnetic metal oxide in the magnetic silica particles is usually at least 60% by weight, and preferably at least 65% by weight, whereas usually at most 95% by weight, and preferably at most 80% by weight. The magnetic silica particles containing less than 60% by weight of a superparamagnetic metal oxide may have insufficient magnetism, requiring prolonged separating operation in practical use. It is difficult to synthesize magnetic silica particles containing more than 95% by weight of a superparamagnetic metal oxide.

The superparamagnetic metal oxide may be produced by any method. For example, it may be synthesized by co-precipitation using water-soluble iron salts and ammonia based on the method of Massart (R. Massart, IEEE Trans. Magn. 1981, 17, 1247), or by a method utilizing oxidation in an aqueous solution of water-soluble iron salts.

The average particle size of the magnetic silica particles is preferably 1 to 5 μm, and more preferably 1 to 3 μm. The magnetic silica particles with an average particle size of smaller than 1 μm tend to require prolonged separating and collecting operations. The magnetic silica particles with an average particle size of greater than 5 μm tend to have a small specific surface area, resulting in a small amount of a substance to be carried (analyte, analog of the analyte, or substance capable of specifically binding to the analyte) and low binding efficiency.

The average particle size of the magnetic silica particles in the present invention is an average value of particle sizes of any 200 magnetic silica particles measured using a scanning electron microscope ("JSM-7000F", JEOL Ltd.).

The average particle size of the magnetic silica particles can be controlled by adjusting the mixing conditions (e.g. shear strength) in production of an oil-in-water emulsion (to be mentioned later) so as to adjust the particle size of the oil-in-water emulsion. The average particle size thereof may be set to a desired value by adjusting the conditions in a water-washing step in the production of magnetic silica particles or usual classification.

The magnetic silica particles in the present invention may be produced as follows, for example. First, a dispersion (A1) or a dispersion (A2) and a solution (B) are mixed to prepare an oil-in-water emulsion; here, the dispersion (A1) contains superparamagnetic metal oxide particles having an average particle size of 1 to 15 nm, an (alkyl)alkoxysilane in an amount of 30 to 500% by weight for 100% by weight of the superparamagnetic metal oxide particles, and a dispersant; the dispersion (A2) contains the same components as in the dispersion (A1) and further contains a water-insoluble organic solvent; and the solution (B) contains water, a water-soluble organic solvent, a nonionic surfactant, and a catalyst for hydrolysis of the (alkyl)alkoxysilane. Then, the (alkyl)alkoxysilane is hydrolyzed and condensed to prepare particles including silica and a superparamagnetic metal oxide included in the silica.

After the hydrolysis and condensation of the (alkyl)alkoxysilane, the product is centrifuged and the resulting solid and liquid portions are separated using a magnet. Then, the obtained solid portion is washed with water or methanol, followed by drying. This process thereby yields magnetic silica particles.

The term "(alkyl)alkoxysilane" used above and to be used below means an alkylalkoxysilane or an alkoxysilane.

The dispersant may be, for example, an organic compound having one or more carboxyl groups in its molecule, an organic compound having one or more sulfo groups in its molecule, or an organic compound having one or more carboxyl groups and one or more sulfo groups in its molecule. Specific examples thereof include the following organic compounds (a-1) to (a-5), and each of these compounds may be used alone, or two or more of these may be used in combination.

(a-1) Organic compounds having two or more carboxyl groups:

C2-C30 aliphatic polycarboxylic acids (e.g. saturated polycarboxylic acids such as oxalic acid, malonic acid, succinic acid, glutaric acid, adipic acid, pimelic acid, suberic acid, azelaic acid, sebacic acid, propane-1,2,3-tricarboxylic acid, citric acid, and dodecanedioic acid, and unsaturated polycarboxylic acids such as maleic acid, fumaric acid, and itaconic acid); C8-C30 aromatic polycarboxylic acids (e.g. phthalic acid, isophthalic acid, terephthalic acid, trimellitic acid, and pyromellitic acid); C5-C30 alicyclic polycarboxylic acids (e.g. cyclobutene-1,2-dicarboxylic acid, cyclopentene-1,2-dicarboxylic acid, furane-2,3-dicarboxylic acid, bicyclo[2,2,1]hept-2-ene-2,3-dicarboxylic acid, and bicyclo[2,2,1]hepta-2,5-diene-2,3-dicarboxylic acid).

(a-2) Organic compounds having two or more sulfo groups:

C1-C30 aliphatic polysulfonic acids (e.g. methionic acid, 1,1-ethanedisulfonic acid, 1,2-ethanedisulfonic acid, 1,1-propanedisulfonic acid, 1,3-propanedisulfonic acid, and polyvinyl sulfonic acid); C6-C30 aromatic polysulfonic acids (e.g. m-benzenedisulfonic acid, 1,4-naphthalenesulfonic acid, 1,5-naphthalenedisulfonic acid, 1,6-naphthalenedisulfonic acid, 2,6-naphthalenedisulfonic acid, 2,7-naphthalenedisulfonic acid, and sulfonated polystyrene), and bis(fluorosulfonyl)imide and C2-C10 bis(perfluoroalkanesulfonyl) imides (e.g. bis(trifluoromethanesulfonyl)imide, bis(pentafluoroethanesulfonyl)imide, bis(nonafluorobutanesulfonyl)imide, pentafluoroethanesulfonyl trifluoromethanesulfonyl imide, trifluoromethanesulfonyl heptafluoropropanesulfonyl imide, and nonafluorobutanesulfonyl trifluoromethanesulfonyl imide).

(a-3) Organic compounds having one or more carboxyl groups and one or more sulfo groups:

C2-C30 sulfocarboxylic acids (e.g. sulfoacetic acid and sulfosuccinic acid); and C7-C30 sulfoaromatic mono- or poly-carboxylic acids (e.g. o-, m-, or p-sulfobenzoic acid, 2,4-disulfobenzoic acid, 3-sulfophthalic acid, 3,5-disulfophthalic acid, 4-sulfoisophthalic acid, 2-sulfoterephthalic acid, 2-methyl-4-sulfobenzoic acid, 2-methyl-3,5-disulfobenzoic acid, 4-propyl-3-sulfobenzoic acid, 4-isopropyl-3-sulfobenzoic acid, 2,4,6-trimethyl-3-sulfobenzoic acid, 2-methyl-5-sulfoterephthalic acid, 5-methyl-4-sulfoisophthalic acid, 5-sulfosalicylic acid, and 3-oxy-4-sulfobenzoic acid).

(a-4) Organic compounds having one carboxyl group:

C1-C30 aliphatic saturated monocarboxylic acids (e.g. formic acid, acetic acid, propionic acid, butyric acid, isobutyric acid, valeric acid, caproic acid, enanthic acid, caprylic acid, pelargonic acid, lauric acid, myristic acid, stearic acid, and behenic acid); C3-C30 aliphatic unsaturated monocarboxylic acids (e.g. acrylic acid, methacrylic acid, and oleic acid); C3-C30 hydroxy aliphatic monocarboxylic acids (e.g. glycolic acid, lactic acid, and tartaric acid); C4-C30 alicyclic monocarboxylic acids (e.g. cyclopropane carboxylic acid, cyclopentane carboxylic acid, and cyclohexane carboxylic acid); C7-C30 aromatic monocarboxylic acids (benzoic acid, cinnamic acid, and naphthoic acid); C7-C20 hydroxy aromatic monocarboxylic acids (e.g. salicylic acid and mandelic acid); and C2-C20 perfluorocarboxylic acids (e.g. trifluoroacetic acid, undecafluorohexanoic acid, tridecafluoroheptanoic acid, perfluorooctanoic acid, pentadecafluorooctanoic acid, heptadecafluorononanoic acid, and nonadecafluorodecanoic acid).

(a-5) Organic compounds having one sulfo group:

C1-C30 aliphatic monosulfonic acids (e.g. methanesulfonic acid, ethanesulfonic acid, propanesulfonic acid, butanesulfonic acid, hexanesulfonic acid, decanesulfonic acid, undecanesulfonic acid, and dodecanesulfonic acid); C6-C30 aromatic monosulfonic acids (e.g. benzenesulfonic acid, p-toluenesulfonic acid, o-toluenesulfonic acid, m-toluenesulfonic acid, 4-dodecylbenzenesulfonic acid, 4-octylbenzenesulfonic acid, and naphthalenesulfonic acid); and C1-C20 perfluoroalkanesulfonic acids (e.g. trifluoromethanesulfonic acid).

C10-C30 organic compounds in the group (a-4) are preferred for good compatibility with an (alkyl)alkoxysilane.

The dispersant is used in an amount of 100 to 2,000% by weight, and preferably 250 to 1,000% by weight, based on the weight of the superparamagnetic metal oxide. The dispersant in an amount of less than 100% by weight tends to have difficulty in dispersing a superparamagnetic metal oxide in a solution of an (alkyl)alkoxysilane. The dispersant in an amount of more than 2,000% by weight tends to cause difficulty in dispersing the particles in an aqueous solution in the following step of preparing an emulsion.

The (alkyl)alkoxysilane to be used may be a compound represented by the following formula (I):

$$R^1_{(4-n)}Si(OR^2)_n \qquad (1)$$

wherein $R^1$ and $R^2$ each may be a C1-C10 monovalent hydrocarbon group optionally substituted by an amino group, a carboxyl group, a hydroxy group, a mercapto group, or a glycidyloxy group.

Examples of the C1-C10 hydrocarbon groups include C1-C10 aliphatic hydrocarbon groups (e.g. a methyl group, an ethyl group, an n- or iso-propyl group, an n- or iso-butyl group, an n- or iso-pentyl group, and a vinyl group); C6-C10 aromatic hydrocarbon groups (e.g. a phenyl group); and C7-C10 aromatic aliphatic groups (e.g. a benzyl group).

In the formula (I), n is an integer of 1 to 4. An alkylalkoxysilane satisfying n=1 requires combination use of an (alkyl)alkoxysilane satisfying n=2 to 4. For good strength of the particles and a satisfactory amount of silanol groups on the particle surface after the reaction, n is preferably 4.

Specific examples of the compound represented by the formula (I) include: alkoxysilanes such as tetramethoxysilane, tetraethoxysilane, tetraisopropoxysilane, and tetrabutoxysilane; alkylalkoxysilanes such as methyltrimethoxysilane and methyltriethoxysilane; alkylalkoxysilanes having an amino-substituted alkyl group such as 3-aminopropyltrimethoxysilane, 3-aminopropyltriethoxysilane, N-2-(aminoethyl)-3-aminopropyltrimethoxysilane, and N-2-(aminoethyl)-3-aminopropyltriethoxysilane; alkylalkoxysilanes having a carboxyl-substituted alkyl group such as 7-carboxyheptyltriethoxysilane and 5-carboxy-pentyltriethoxysilane; alkylalkoxysilanes having a hydroxy-substituted alkyl group such as 3-hydroxypropyltrimethoxysilane and 3-hydroxypropyltriethoxysilane; alkylalkoxysilanes having a mercapto-substituted alkyl group such as 3-mercaptopropyltrimethoxysilane and 3-mercaptopropyltriethoxysilane; and alkylalkoxysilanes having a glycidyloxy-substituted alkyl group such as 3-glycidyloxypropyltrimethoxysilane and 3-glycidyloxypropyltriethoxysilane.

Each of these (alkyl)alkoxysilanes may be used alone, or two or more of these may be used in combination.

The (alkyl)alkoxysilane is usually used in an amount of 30 to 500% by weight, and preferably 40 to 200% by weight, for 100% by weight of the superparamagnetic metal oxide. If the amount of the (alkyl)alkoxysilane is less than 30% by weight, the surface of the superparamagnetic metal oxide may be less likely to be uniformly covered. If the amount thereof is more than 500% by weight, the proportion of the superparamagnetic metal oxide is so small that collection of the particles by the magnetic force may take a long time.

The water is preferably used in an amount of 500 to 3,000% by weight, and particularly preferably 800 to 2,000% by weight, for 100% by weight of the superparamagnetic metal oxide.

Examples of the water-insoluble organic solvent include C6-C16 aromatic hydrocarbon solvents (e.g. toluene and xylene) and C5-C16 aliphatic hydrocarbon solvents (e.g. n-heptane, n-hexane, cyclohexane, n-octane, decane, and decahydronaphthalene) having a solubility in water of 0.1 g/100 g of water or lower at 25° C. Each of these may be used alone, or two or more of these may be used in combination.

The water-insoluble organic solvent is used in an amount of 200 to 1,000% by weight, and preferably 250 to 500% by weight, for 100% by weight of the superparamagnetic metal oxide. The organic solvent in an amount of less than 200% by weight tends to cause poor dispersibility of the superparamagnetic metal oxide. The organic solvent in an amount of more than 1,000% by weight tends to cause an uneven particle size of the magnetic silica particles.

Examples of the water-soluble organic solvent include C1-C3 alcohols (e.g. methanol, ethanol, and n- or isopropanol); C2-C9 glycols (e.g. ethylene glycol and diethylene glycol); amides (e.g. N-methylpyrrolidone); ketones (e.g. acetone); cyclic ethers (e.g. tetrahydropyran and tetrahydropyran); lactones (e.g. γ-butyrolactone); sulfoxides (e.g. dimethyl sulfoxide); and nitriles (e.g. acetonitrile) having a solubility in water of 100 g/100 g of water or higher at 25° C.

C1-C4 alcohols are preferred for a uniform particle size of the magnetic silica particles.

Each of the water-soluble organic solvents may be used alone, or two or more of these may be used in combination.

The water-soluble organic solvent is preferably used in an amount of 100 to 500% by weight for 100% by weight of water.

Examples of the nonionic surfactant include nonionic surfactants including alkylene oxide adducts of fatty alcohols (hereinafter, alkylene oxide is abbreviated as AO); 1 to 20 mol ethylene oxide and/or 1 to 20 mol propylene oxide adducts of C8-C24 fatty alcohols (e.g. decyl alcohol, dodecyl alcohol, palm oil alkyl alcohols, octadecyl alcohol, and oleyl alcohol) (hereinafter, ethylene oxide is abbreviated as EO; propylene oxide is abbreviated as PO; adducts include block adducts and/or random adducts, the same shall apply to the following); AO adducts of alkylphenols having C6-C24 alkyl; 1 to 20 mol EO and/or 1 to 20 mol PO adducts of octylphenol or nonylphenol, EO adducts of polypropylene glycol and PO adducts of polyethylene glycol; AO adducts of fatty acids such as Pluronic-series surfactants; 1 to 20 mol EO and/or 1 to 20 mol PO adducts of C8-C24 fatty acids (e.g. decanoic acid, lauric acid, myristic acid, palmitic acid, stearic acid, oleic acid, and palm oil fatty acids) and polyhydric alcohol-type nonionic surfactants; EO and/or PO adducts of C3-C36 polyhydric alcohols having two to eight hydroxy groups (e.g. glycerin, trimethylol propane, pentaerythritol, sorbit, and sorbitan); fatty acid esters of the above polyhydric alcohols and EO adducts thereof (e.g. TWEEN® 20 and TWEEN® 80); alkylglycosides (e.g. N-octyl-β-D-maltoside, n-dodecanoyl sucrose, and n-octyl-β-D-glucopyranoside); and sugar fatty acid esters, fatty acid alkanolamides, and AO adducts thereof (e.g. polyoxyethylene fatty acid alkanolamides). Each of these may be used alone, or two or more of these may be used in combination.

The nonionic surfactant is preferably used in an amount of 100 to 1,000% by weight, and particularly preferably 300 to 500% by weight, for 100% by weight of the superparamagnetic metal oxide. The nonionic surfactant in an amount of less than 100% by weight or more than 1,000% by weight tends to give unstable emulsion, resulting in a wide particle size distribution of particles to be obtained.

The aqueous solution containing a nonionic surfactant is preferably used in an amount of 1,000 to 10,000% by weight, and particularly preferably 1,500 to 4,000% by weight, for 100% by weight of the superparamagnetic metal oxide. The aqueous solution in an amount of less than 1,000% by weight or in an amount of more than 10,000% by weight tends to give unstable emulsion, resulting in wide particle size distribution of particles to be obtained.

The catalyst for hydrolysis of an (alkyl)alkoxysilane may be a Lewis acid or hydrochloric acid, for example. Specific examples thereof include inorganic acids such as hydrochloric acid, organic acids such as acetic acid, inorganic basic compounds such as ammonia, and amine compounds such as ethanol amine.

The catalyst for hydrolysis is preferably used in an amount of 0.01 to 100% by weight, and particularly preferably 0.2 to 50% by weight, based on the amount of the (alkyl)alkoxysilane.

The dispersion (A1) or the dispersion (A2) and the solution (B) may be collectively mixed using an apparatus to be mentioned later. For a uniform particle size of the magnetic silica particles, it is preferable to dropwise add the dispersion (A1) or the dispersion (A2) to the solution (B) under stirring.

The apparatus for mixing the dispersion (A1) or dispersion (A2) and the solution (B) may be any of commercially available emulsifying apparatuses and dispersing apparatuses, including: batch-type emulsifying apparatuses such as Homogenizer (IKA), Polytron (KINEMATICA AG), and TK AUTO HOMO MIXER (Tokushu Kika Kogyo Co., Ltd.); continuous-type emulsifying apparatuses such as EBARA MILDER (EBARA CORP.), TK FILMIX, TK PIPELINE HOMO MIXER (Tokushu Kika Kogyo Co., Ltd.), colloid mill (Shinko Pantec Co., Ltd.), CLEARMIX (M Technique Co., Ltd.), slasher, trigonal wet-type crusher (Mitsui Miike Chemical Engineering Machinery, Co., Ltd.), CAVITRON (EUROTEC. CO., LTD.), and fine flow mill (Pacific Machinery & Engineering Co., Ltd.); high-pressure emulsifying apparatuses such as Microfluidizer (MIZUHO Industrial CO., LTD.), Nanomizer (NANOMIZER Inc.), and APV GAULIN (Gaulin); membrane emulsifying apparatuses such as membrane emulsifier (REICA Co., Ltd.); vibration-type emulsifying apparatuses such as VIVRO MIXER (REICA Co., Ltd.); and ultrasonic emulsifying apparatuses such as ultrasonic homogenizer (Branson Ultrasonics Corp.). APV GAULIN, Homogenizer, TK AUTO HOMO MIXER, EBARA MILDER, TK FILMIX, TK PIPELIME HOMO MIXER, and CLEARMIX are preferred for uniform particle size.

The (alkyl)alkoxysilane is preferably hydrolyzed and condensed at 25° C. to 100° C., and still more preferably 45° C. to 60° C. The reaction time thereof is preferably 0.5 to 5 hours, and still more preferably 1 to 2 hours.

With respect to the magnetic silica particles in the present invention, the superparamagnetic metal oxide is included in silica and does not exist on the particle surface. Thus, the magnetic silica particles can immobilize, on the surface thereof, a large amount of an analyte, an analog of the analyte, or a substance capable of specifically binding to the analyte.

An analyte, an analog of the analyte, or a substance capable of specifically binding to the analyte (hereinafter, these substances may also collectively be referred to as the substance to be immobilized) may be immobilized on the magnetic silica particles in the present invention by, for example, physically adsorbing the substance to be immobilized on the magnetic silica particles. For more efficient immobilization of the substance to be immobilized, preferably, at least one organic compound selected from the group consisting of glutaraldehyde, albumin, carbodiimide, streptavidin, biotin, and functional group-containing alkylalkoxysilanes is bound to the surface of the magnetic silica particles, and the substance to be immobilized is immobilized on the magnetic silica particles via the above organic compound. More preferable among these organic compounds are functional group-containing alkylalkoxysilanes because of binding of a specific substance to be immobilized.

Examples of the functional group in the alkylalkoxysilane include an amino group, a carboxyl group, a hydroxy group, a mercapto group, and a glycidyloxy group. The alkylalkoxysilane may have different functional groups in its molecule.

The functional group-containing alkylalkoxysilane may be bound to the surface of the magnetic silica particles by a method using the aforementioned alkylalkoxysilane having an alkyl group substituted by an amino group, a carboxyl group, a hydroxy group, a mercapto group, or a glycidyloxy group as an (alkyl)alkoxysilane in production of the magnetic silica particles, or by a method including: preparing magnetic silica particles with an (alkyl)alkoxysilane having none of these substituents; and then treating the magnetic silica particles with an alkylalkoxysilane having an alkyl group substituted by an amino group, a carboxyl group, a hydroxy group, a mercapto group, or a glycidyloxy group.

One specific example of the latter method includes a method in which magnetic silica particles are dispersed in a solvent so as to give a concentration of 1 to 50% by weight; a solution of an alkylalkoxysilane having an alkyl group substituted by an amino group, a carboxyl group, a hydroxy group, a mercapto group, or a glycidyloxy group is added to the dispersion; and the hydrolysis and condensation are performed for one or more hours at room temperature.

The solvent in this method is appropriately selected depending on the solubility of an alkylalkoxysilane to be used. For example, water or a water/alcohol mixed solvent is preferred for a water-soluble alkylalkoxysilane having an alkyl group substituted by an amino group, a carboxyl group, a hydroxy group, or a mercapto group; butyl acetate is preferred for a slightly water-soluble alkylalkoxysilane having an alkyl group substituted by a glycidyloxy group.

The alkylalkoxysilane having an alkyl group substituted by an amino group, a carboxyl group, a hydroxy group, a mercapto group, or a glycidyloxy group is preferably used in an amount of 0.1 to 5% by weight based on the amount of the magnetic silica particles before treatment. The alkylalkoxysilane in an amount of less than 0.1% by weight may introduce an insufficient number of functional groups. The alkylalkoxysilane in an amount of more than 5% by weight tends to have a lower effect of increasing the number of functional groups to be introduced onto the particle surface.

Glutaraldehyde, albumin, carbodiimide, streptavidin, or biotin may be bound to the surface of the magnetic silica particles by any method. For example, binding may be achieved as follows.

Glutaraldehyde having an aldehyde group and biotin having a carboxyl group can be bound to the surface of the magnetic silica particles by reaction with the magnetic silica particles having an amino group-containing alkylalkoxysilane bound to the particle surface. Albumin and streptavidin each having an amino group, and carbodiimide having a carbodiimide group can be bound to the surface of the magnetic silica particles by reaction with the magnetic silica particles having a carboxyl group-containing alkylalkoxysilane.

The method of assaying an analyte of the present invention may be performed in conformity with the methods usually performed in this field, except that the magnetic silica particles in the present invention are used in the assay method of the present invention. Examples of such methods include a sandwich method and a competitive method disclosed in documents (e.g. "Koso Meneki Sokutei-Ho" second edition, edited by Eiji ISHIKAWA, et al., IGAKU-SHOIN Ltd., 1982), and a measurement method disclosed in JP H06-130063 A.

For example, the sandwich method may be performed as follows: an analyte-containing sample, magnetic silica particles having a substance capable of specifically binding to the analyte (analyte-binding substance) immobilized on the surface, and an analyte-binding substance labeled by a label (labeled analyte-binding substance) are brought into contact with each other to form a complex (labeled complex) of the analyte-binding substance, the analyte in the sample, and the labeled analyte-binding substance on the magnetic silica particles; magnetic silica particles carrying the labeled complex are B/F-separated; the amount of the label in the labeled complex is measured; and the analyte in the sample is assayed based on the resulting amount of the label.

Specifically, for example, an analyte-containing sample and magnetic silica particles having an analyte-binding substance immobilized on the surface thereof are brought into contact with each other to form a complex of the analyte-binding substance and the analyte on the surface of the magnetic silica particles; the complex is brought into contact with a labeled analyte-binding substance to form a complex (labeled complex) of the analyte-binding substance, the analyte in the sample, and the labeled analyte-binding substance immobilized on the magnetic silica particles; the magnetic silica particles carrying the labeled complex are B/F-separated; the amount of the label in the labeled complex is measured; and the analyte in the sample is assayed based on the resulting amount of the label. In this method, the analyte in the sample and the magnetic silica particles having an analyte-binding substance immobilized thereon are first reacted and then the labeled analyte-binding substance is reacted thereto. Still, the labeled analyte-binding substance and the analyte in the sample may be first reacted and then the magnetic silica particles having the analyte-binding substance immobilized thereon may be reacted thereto, or these three components may be reacted with each other at the same time.

The B/F separation in the sandwich method means separation of a labeled complex and a labeled analyte-binding substance that do not involve in the formation of the labeled complex. Specifically, the B/F separation means separation of an analyte-binding substance immobilized on magnetic silica particles, a complex of the analyte-binding substance immobilized on the magnetic silica particles, and the analyte in the sample, and a labeled complex, from the other components (e.g. components other than the analyte in the sample, a labeled analyte-binding substance that does not involve in the formation of the labeled complex).

The B/F separation is an essential step after the formation of a labeled complex. This may be performed after the formation of a complex of the analyte-binding substance immobilized on the surface of the magnetic silica particles and the analyte in the sample.

In one embodiment of the competitive method, an analyte-containing sample, a substance labeled by a label and specifically binding to the analyte (labeled analyte-binding substance), and magnetic silica particles having an analyte or an analog of the analyte immobilized on the surface thereof are brought into contact with each other to form a complex (labeled complex) of the analyte or its analog and the labeled analyte-binding substance on the magnetic silica particles; the magnetic silica particles carrying the labeled complex are B/F-separated; the amount of the label in the labeled complex is measured; and the analyte in the sample is assayed based on the resulting amount of the label.

Specifically, for example, an analyte-containing sample, a labeled analyte-binding substance, and magnetic silica particles immobilizing an analyte or its analog are brought into contact with each other, so that the labeled analyte-binding substance is competitively reacted with the analyte in the sample and the analyte or its analog on the magnetic silica particles to form a complex (labeled complex) of the analyte or its analog and the labeled analyte-binding substance on the magnetic silica particles; the magnetic silica particles carrying the labeled complex are B/F-separated; the amount of the label in the labeled complex is measured; and the analyte in the sample is assayed based on the resulting amount of the label. In this method, an analyte, a labeled analyte-binding substance, and magnetic silica particles immobilizing the analyte or its analog are competitively reacted at the same time. Still, the analyte in the sample and the magnetic silica particles immobilizing the analyte or its analog may be first brought into contact with each other and the labeled analyte-binding substance may be then competitively reacted therewith, or the analyte and the labeled analyte-binding substance may be first brought into contact with each other and the magnetic silica particles immobilizing the analyte or its analog may be then competitively reacted therewith.

The B/F separation in the competitive method means separation of the labeled complex from the other components (a labeled analyte-binding substance and a complex of the labeled analyte-binding substance and the analyte in the sample) that do not involve in the formation of the labeled complex. Specifically, the B/F separation means separation of magnetic silica particles immobilizing an analyte or its analog and a complex (labeled complex) of the magnetic silica particles immobilizing the analyte or its analog and the labeled analyte-binding substance from the other components (e.g. components other than the analyte in the sample, a labeled analyte-binding substance, and a complex of the analyte in the sample and the labeled analyte-binding substance).

In another embodiment of the competitive method, an analyte-containing sample, an analyte or its analog labeled by a label (labeled analyte or its analog), and magnetic silica particles immobilizing an analyte-binding substance are brought into contact with each other to form a complex (labeled complex) of the analyte-binding substance and the labeled analyte or its analog on the magnetic silica particles; the magnetic silica particles carrying the labeled complex are B/F-separated; the amount of the label in the labeled complex is measured; and the analyte in the sample is assayed based on the resulting amount of the label.

Specifically, for example, an analyte-containing sample, a labeled analyte or its analog, and magnetic silica particles immobilizing an analyte-binding substance are brought into contact with each other, so that the analyte in the sample and the labeled analyte or its analog are competitively reacted with the analyte-binding substance on the magnetic silica particles to form a complex (labeled complex) of the analyte-binding substance and the labeled analyte or its analog on the magnetic silica particles; the magnetic silica particles carrying the labeled complex are B/F-separated; the amount of the label in the labeled complex is measured; and the analyte in the sample is assayed based on the resulting amount of the label. In this competitive method, the analyte, the labeled analyte or its analog, and the magnetic silica particles immobilizing the analyte-binding substance are competitively reacted with each other at the same time. Still, the analyte in the sample and the magnetic silica particles immobilizing the analyte-binding substance may be first brought into contact with each other and the labeled analyte or its analog may be then competitively reacted therewith, or the labeled analyte or its analog and the magnetic silica particles immobilizing the analyte-binding substance may be first brought into contact with each other and the analyte in the sample may be then competitively reacted therewith.

The B/F separation in the above competitive method means separation of the labeled complex from the other components (e.g. a labeled analyte or its analog) that do not involve in the formation of the labeled complex. Specifically, the B/F separation means separation of the magnetic silica particles immobilizing an analyte-binding substance, a complex of the magnetic silica particles immobilizing an analyte-binding substance and the analyte in the sample, and the complex of the magnetic silica particles immobilizing the analyte-binding substance and the labeled analyte or its analog from the other components (e.g. components other than the analyte in the sample, a labeled analyte or its analog that do not involve in the formation of the labeled complex).

In the case that the analyte is an enzyme, the analyte may be assayed by a method utilizing an enzyme activation method other than the sandwich method and the competitive method. For example, the analyte may be assayed as follows: an analyte-containing sample and magnetic silica particles having an analyte-binding substance (e.g. a substance capable of binding to an enzyme, such as an antibody) immobilized on the surface thereof are brought into contact with each other to form a complex of the enzyme and the analyte-binding substance on the magnetic silica particles; the magnetic silica particles carrying the complex are B/F-separated; a substrate corresponding to the enzyme, or a substrate corresponding to the enzyme and a color coupler, and optionally a coupling enzyme, are added to the system; and the amount of the enzyme in the sample is measured on the basis of the change in the substrate or the coloring result of the color coupler. The substrate, the color coupler, and the coupling enzyme may be any of known ones. In the case that the enzyme is peroxidase, hydrogen peroxide and a luminol reagent can be used. The amounts thereof are within the range as usual in this field. The B/F separation in this method means separation of a complex of an analyte and magnetic silica particles immobilizing an analyte-binding substance from the other components (e.g. components other than the analyte in the sample).

In the method of assaying an analyte of the present invention, a sample, magnetic silica particles, a labeled analyte-binding substance, a labeled analyte or its analog, and the like are brought into contact with each other such that the magnetic silica particles are dispersed by usual treatment such as stirring or mixing. The reaction time may appropriately be adjusted depending on the analyte, the analyte-binding substance to be used, and the treating process such as the sandwich method or the competitive method. The reaction time is usually 1 to 10 minutes, and preferably 1 to 5 minutes.

The B/F separation in the method of assaying an analyte of the present invention may be performed as follows: utilizing the magnetism of magnetic silica particles, the magnetic silica particles are collected using a magnet from the outside of a reaction vessel and the reaction solution is discharged; a washing solution is added and the magnet is removed; and the magnetic silica particles are mixed and dispersed into the solution and the particles are washed. This process may be repeated one to three times. The washing solution may be any one usually used in this field.

Examples of the label for labeling the analyte-binding substance and the analyte or its analog include: enzymes used in enzyme immunoassay (EIA), such as alkaline phosphatase, β-galactosidase, peroxidase, microperoxidase, glucose oxidase, glucose-6-phosphate dehydrogenase, malate dehydrogenase, luciferase, tyrosinase, and acid phosphatase; radioisotopes used in radioimmunoassay (RIA), such as $^{99m}$Tc, $^{131}$I, $^{125}$I, $^{14}$C, $^{3}$H, and $^{32}$P; and fluorescent substances, luminous substances, ultraviolet-absorbing substances, and compounds having characteristics as spin-labeling agents typified by oxyl group-containing compounds, used in fluorescent immunoassay (FIA); the fluorescent substances including fluorescein, dansyl, fluorescamine, coumarin, naphthylamine, derivatives thereof, and green fluorescent protein (GFP), the luminous substances including luciferin, isoluminol, luminol, and bis(2,4,6-trifluorophenyl)oxalate, the ultraviolet-absorbing substances including phenol, naphthol, anthracene, and derivatives thereof, and the compounds having characteristics as spin-labeling agents typified by oxyl group-containing compounds including 4-amino-2,2,6,6-tetramethylpiperidin-1-oxyl, 3-amino-2,2,5,5-tetramethylpyrrolidin-1-oxyl, and 2,6-di-t-butyl-α-(3,5-di-t-butyl-4-oxo-2, 5-cyclohexadien-1-ylidene)-p-trioxyl.

Enzymes and fluorescent substances are preferred, alkaline phosphatases, peroxidase, and glucose oxidase are more preferred, and peroxidase is particularly preferred, because of good sensitivity and other factors.

The aforementioned labels may be bound to an analyte-binding substance and an analyte or its analog by a method usually performed in this field, such as known labeling techniques used in known EIA, RIA, or FIA (e.g. glutaraldehyde technique, periodic acid technique, maleimide technique, and pyridyl disulfide technique, disclosed in "Ikagaku Jikken-Ho Koza", vol. 8, supervised by Yuichi YAMAMURA, first impression, Nakayama Shoten Co., Ltd., 1971; "Zusetsu Keiko Kotai-Ho", Akira KAWAOI, first impression, I-NET Corp., 1983; "Koso Meneki Sokutei-Ho", edited by Eiji ISHIKAWA, Tadashi KAWAI, Kiyoshi Miyai, second impression, Igaku-Shoin Ltd., 1982).

The amount of the label to be used is not unconditionally determined because the amount depends on the type of label. In the case of a peroxidase label, the analyte-binding substance and the label are used at a ratio by mole of, usually 1:1 to 1:20, preferably 1:1 to 1:10, and more preferably 1:1 to 1:2, contained in a buffer usually used in this field, such as Tris buffer, phosphate buffer, veronal buffer, borate buffer, or Good's buffer. Examples of the buffer include those usually used in this field, such as Tris buffer, phosphate buffer, veronal buffer, borate buffer, and Good's buffer. The pH thereof is within a range that does not suppress the antigen-antibody interaction, and is usually 5 to 9. The buffer may contain any of stabilizers (e.g. albumin, globulin, water-soluble gelatin, and polyethylene glycol), surfactants, and saccharides that do not suppress the target antigen-antibody interaction.

The label or its activity may be assayed by, for example, radioimmunoassay (RIA), enzyme immunoassay (EIA), fluorescent immunoassay (FIA), chemiluminescence immunoassay (CLIA), or chemiluminescence enzyme immunoassay (CLEIA). EIA, CLIA, and CLEIA are preferred, and CLEIA is more preferred, because of good sensitivity in a short-time immunoassay.

In the case of assaying AFP by the sandwich method, for example, the assay method of the present invention can be performed as follows.

For example, a reaction vessel is charged with 10 to 25 µL of an AFP-containing sample and 40 to 50 µL of a buffer (e.g. a phosphate buffer) containing 0.1 to 1 mg/mL of the magnetic silica particles in the present invention immobilizing an anti-AFP antibody (a magnetic silica particle-containing reagent). The reaction solution is stirred and the magnetic silica particles are dispersed therein, so that the anti-AFP antibody immobilized on the magnetic silica particles and the AFP are brought into contact and reacted with each other to form a complex. Next, the magnetic silica particles are collected using a magnet from the outside of the reaction vessel. The reaction solution is then discharged, and a washing solution (e.g. a physiological saline solution) is added thereto. Then, the magnet is removed, and the magnetic silica particles are dispersed and washed. This operation may be repeated one to three times. This washing operation may be eliminated in the case that the reaction is performed using an anti-AFP antibody labeled (hereinafter, also referred to as the labeled reagent) with a peroxidase (hereinafter, also abbreviated as POD) derived from horseradish, for example, in the presence of a remaining sample or magnetic silica particle-containing reagent. Then, a labeled reagent is added and the reaction solution is stirred so that the magnetic silica particles are dispersed. Thereby, the POD-labeled anti-AFP antibody and the complex are reacted and bound to each other. In the same manner as in the washing, a washing solution (e.g. a physiological saline solution) is added so that the particles are dispersed and washed. Finally, luminol and hydrogen peroxide are added and the integrated chemiluminescent intensity in one second is measured using a chemiluminescent detector and, on the basis of this measured value, the AFP content in the sample is calculated. In this case, the AFP content in the sample can be calculated easily using a standard curve which shows the relationship between the AFP content and the integrated chemiluminescent intensity in one second. The standard curve may be preliminarily drawn using a standard AEP-containing solution as a sample in the same manner as mentioned above.

The reagent of the present invention contains the magnetic silica particles in the present invention, and is used in the above assay method. Specific examples thereof include buffers containing the magnetic silica particles in the present invention, and the buffers are preferably those usually used in immunoassay. Examples thereof include 1,4-piperazinediethanesulfonic acid/sodium hydroxide buffer, MOPS (3-(N-morpholino)propanesulfonic acid)/sodium hydroxide buffer, triethanolamine/hydrochloric acid buffer, and PBS (phosphate buffer).

The buffer preferably contains a buffering agent at a concentration of 1 to 500 mM, more preferably 5 to 300 mM, and particularly preferably 10 to 200 mM.

The unit "mM" used above and to be used below means the concentration (mmol/L) at 25° C.

The amount of the magnetic silica particles is not particularly limited and may appropriately be adjusted depending on the type of an analyte-binding substance or an analog of the analyte to be used and the type of an analyte, for example.

The reagent of the present invention is preferably in the form that the magnetic silica particles in the present invention are dispersed in a buffer.

In addition to the reagent containing the magnetic silica particles in the present invention, the reagent of the present invention may further include a reagent containing a substance capable of specifically binding to an analyte labeled by a label, or a reagent containing an analyte or its analog labeled by a label (hereinafter, also referred to as a labeled reagent). The label to be used here may be selected from those listed above in the section of the assay method of the present invention, and preferable labels are also the same ones mentioned above.

The labeled reagent may further contain a buffer in addition to the substance capable of specifically binding to an analyte labeled by a label or the analyte or its analog labeled by a label. The buffer used in the labeled reagent is preferably one usually used in immunoassay. Examples thereof include the buffers used in the above magnetic silica particle-containing reagents. The concentration of a buffering agent in the buffer is also the same as that in the reagent containing the magnetic silica particles.

In addition to the reagent containing the magnetic silica particle in the present invention and the labeled reagent, the reagent of the present invention may further include a chemiluminescence reagent. The chemiluminescence reagent is selected depending on the type of the label. For example, with POD as a label, the chemiluminescence reagent includes a first chemiluminescence reagent essentially consisting of a 2,3-dihydro-1,4-phthalazinedione compound and a chemiluminescence enhancer, and a second chemiluminescence reagent essentially consisting of an oxidant and water.

Examples of the 2,3-dihydro-1,4-phthalazinedione compound include known 2,3-dihydro-1,4-phthalazinedione compounds disclosed in JP H02-291299 A, JP H10-319015 A, and JP 2000-279196 A, and mixtures thereof.

Preferable are luminol, isoluminol, N-aminohexyl-N-ethyl isoluminol (AHEI), N-aminobutyl-N-ethyl isoluminol (ABEI), and metal salts thereof (e.g. alkali metal salts). More preferable are luminol and its metal salts, and particularly preferable is luminol sodium salt.

The concentration of the 2,3-dihydro-1,4-phthalazinedione compound in the chemiluminescence reagent may appropriately be adjusted depending on the type, the assay method to be performed, the assay conditions, and the like. The concentration is preferably 0.5 to 80 mM, more preferably 1.8 to 40 mM, and particularly preferably 3.5 to 21 mM, because of a good chemiluminescence enhancing effect and storage stability.

Examples of the chemiluminescence enhancer include known chemiluminescence enhancers disclosed in JP S59-500252 A, JP S59-171839 A, and JP H02-291299 A and mixtures thereof.

Phenols are preferred because of a good chemiluminescence enhancing effect. More preferable are P-iodophenol, 4-(cyanomethylthio)phenol, and 4-cyanomethylthio-2-chlorophenol, and particularly preferable is 4-(cyanomethylthio) phenol.

The concentration of the chemiluminescence enhancer in the chemiluminescence reagent may appropriately be adjusted depending on the type thereof, the assay method to be performed, the assay conditions, and the like. The concentration thereof is preferably 0.1 to 15 mM, more preferably 0.3 to 7.0 mM, and particularly preferably 0.6 to 3.4 mM, because of a good chemiluminescence enhancing effect and storage stability.

In addition to the 2,3-dihydro-1,4-phthalazinedione compound and the chemiluminescence enhancer, the first chemiluminescence reagent may further contain a buffer and/or a chelating agent.

Examples of the buffer include known buffers disclosed in JP H10-319015 A and JP 2003-279489 A.

Preferred are 3-[4-(2-hydroxyethyl)-1-piperazinyl]propanesulfonic acid/sodium hydroxide buffer, 2-hydroxy-3-[4-(2-hydroxyethyl)-1-piperazinyl]propanesulfonic acid monohydrate/sodium hydroxide buffer, and piperazinyl-1,4-bis(2-hydroxy-3-propanesulfonic acid) dihydrate/sodium hydroxide buffer; more preferred are 3-[4-(2-hydroxyethyl)-1-piperazinyl]propanesulfonic acid/sodium hydroxide buffer and 2-hydroxy-3-[4-(2-hydroxyethyl)-1-piperazinyl]propanesulfonic acid monohydrate/sodium hydroxide buffer; and particularly preferred is 3-[4-(2-hydroxyethyl)-1-piperazinyl]propanesulfonic acid/sodium hydroxide buffer, because of a good chemiluminescence enhancing effect and storage stability.

The concentration of the buffering agent in the buffer is preferably 1 to 500 mM, more preferably 5 to 300 mM, and particularly preferably 10 to 200 mM, because of a good chemiluminescence enhancing effect and storage stability.

Examples of the chelating agent include known chelating agents disclosed in JP H09-75099A and JP 2003-279489A.

Tetradentate chelating agents are preferred because of a good chemiluminescence enhancing effect and storage stability. More preferred are ethylenediaminetetraacetic acid (EDTA) and salts thereof (e.g. disodium ethylenediaminetetraacetate, trisodium ethylenediaminetetraacetate, tetrasodium ethylenediaminetetraacetate, dipotassium ethylenediaminetetraacetate, tripotassium ethylenediaminetetraacetate) and trans-1,2-diaminocyclohexane-N,N,N',N'-tetraacetic acid (CyDTA), and particularly preferred are ethylenediaminetetraacetate (EDTA) and salts thereof.

In the case of using a chelating agent, the amount thereof is preferably 0.001 to 4% by weight, more preferably 0.01 to 2% by weight, and particularly preferably 0.05 to 1% by weight, based on the amount of the 2,3-dihydro-1,4-phthalazinedione compound because of a good chemiluminescence enhancing effect and storage stability.

The first chemiluminescence reagent is preferably in the form of liquid, and is preferably alkaline because of favorable fluorescence intensity of enzymes. The first reagent preferably has a pH of 7 to 11, and more preferably 8 to 10. The pH is measured in conformity with JIS K0400-12-10:2000 (measurement temperature: 25° C.)

The first chemiluminescence reagent is easily prepared by uniformly mixing a 2,3-dihydro-1,4-phthalazinedione compound, a chemiluminescence enhancer, and optionally a buffer and/or a chelating agent.

Examples of the oxidant in the second chemiluminescence reagent include aqueous solutions of known oxidants disclosed in JP H08-261943 A and JP 2000-279196 A (e.g. inorganic peroxides such as hydrogen peroxide, sodium perborate, and potassium perborate; organic peroxides such as dialkyl peroxides and acyl peroxides; peroxy acid compounds such as peroxysulfuric acid and peroxyphosphoric acid).

A hydrogen peroxide aqueous solution, a sodium perborate aqueous solution, and a potassium perborate aqueous solution are preferred, and a hydrogen peroxide aqueous solution is more preferred, because of good storage stability.

The concentration of the oxidant in the second chemiluminescence reagent may appropriately be adjusted depending on the type thereof, the assay method to be performed, the assay conditions, and the like. For example, the concentration thereof is preferably 0.5 to 40 mM, more preferably 1 to 20 mM, and particularly preferably 2.5 to 10 mM, because of a good chemiluminescence enhancing effect.

The water in the second chemiluminescence reagent may be distilled water, reverse osmosis water, or deionized water. Distilled water and deionized water are preferred, and deionized water is more preferred, because of a good chemiluminescence enhancing effect and storage stability.

The second chemiluminescence reagent may further contain a chelating agent in addition to the oxidant and the water.

The chelating agent to be used here may be selected from those listed above as the chelating agents for the first reagent, and preferable chelating agents are also the same ones as mentioned above.

In the case of using a chelating agent, the amount thereof is preferably 0.2 to 100% by weight, more preferably 0.5 to 20% by weight, and particularly preferably 1 to 10% by weight, based on the amount of the oxidant because of a good chemiluminescence enhancing effect and storage stability.

The second chemiluminescence reagent can be easily prepared by uniformly mixing an oxidant, water, and optionally a chelating agent.

EXAMPLES

The present invention will be more specifically described below referring to examples. The present invention is not limited to the examples. In the following, "%" means "% by weight" and "part(s)" means "part(s) by weight", unless otherwise mentioned.

Production Example 1

A reaction container was charged with iron (III) chloride hexahydrate (2.7 parts), iron (II) chloride tetrahydrate (1.0 part), and water (375 parts). The solid portion was dissolved into the liquid portion, and the solution was heated up to 50° C. A mixed solution of 25% ammonia water (3.8 parts) and water (100 parts) was dropwise added to the heated solution over one hour while maintaining the temperature at 50° C. to 55° C. under stirring. The mixture was stirred for another one hour after the dropwise addition, and then oleic acid (10.5 parts) was added and the mixture was stirred for another two hours. The mixture was cooled down to room temperature and decanted for solid/liquid separation. The obtained oleic acid-adsorbing magnetite particles were washed with water (50 parts) three times, and the oleic acid-adsorbing magnetite particles were then charged into a container. Decane (5.7 parts) and tetraethoxysilane (2.2 parts) were added thereto and mixed to prepare a dispersion (A2-1).

A reaction container was charged with 25% ammonia water (39.0 parts), isopropanol (55.4 parts), sorbitan monooleate (2.9 parts) ("IONET S-80", Sanyo Chemical Industries, Ltd.), and (C16-C18) polyoxyethylene alkyl ether ("EMULMIN 200", Sanyo Chemical Industries, Ltd., amount in moles of polyoxyethylene added: 20 mol) (2.0 parts). The components were mixed using CLEARMIX (M Technique Co., Ltd.) and the mixture was heated up to 50° C. The dispersion (A2-1) was dropwise added over one hour while stirring the mixture using CLEARMIX at a rotation rate of 6,000 rpm, and the components were reacted for one hour at 50° C. After the reaction, the mixture was centrifuged at 2,000 rpm for five minutes, and a supernatant containing fine particles was removed. Water (50 parts) was added to the obtained solid phase so that the particles were dispersed therein. The dispersion was centrifuged at 1,000 rpm for 10 minutes, and the supernatant containing fine particles was removed. This operation was repeated 10 times. Water (50 parts) was added to the obtained solid phase so that the particles were dispersed therein. The dispersion was centrifuged at 500 rpm for five minutes, and particles with a large particle size were precipitated. Then, a supernatant (1) containing particles having a target particle size was collected. Water (50 parts) was added to the remaining solid phase and the mixture was centrifuged at 500 rpm for five minutes. Then, a supernatant (2) was collected. This operation was repeated twice, and particles having a target particle size in the solid phase were collected. With respect to the supernatants (1) and (2), the particles were collected using a magnet. The collected particles were dried at 80° C. for eight hours, thereby preparing magnetic silica particles (S1).

Production Example 2

Magnetic silica particles (S2) were prepared in the same manner as in Production Example 1 except that the rotation rate of CLEARMIX in the emulsification was 7,500 rpm instead of 6,000 rpm.

Production Example 3

Magnetic silica particles (S3) were prepared in the same manner as in Production Example 1 except that the amount of the tetraethoxysilane was 0.5 parts instead of 2.2 parts.

Production Example 4

Magnetic silica particles (S4) were prepared in the same manner as in Production Example 3 except that the rotation rate of CLEARMIX in the emulsification was 7,500 rpm instead of 6,000 rpm.

Production Example 5

Magnetic silica particles (S5) were prepared in the same manner as in Production Example 1 except that the amount of the water mixed with the 25% ammonia water (3.8 parts) in the production of magnetite particles was 33.8 parts instead of 100 parts.

Production Example 6

Magnetic silica particles (S6) were prepared in the same manner as in Production Example 5 except that the rotation rate of CLEARMIX in the emulsification was 7,500 rpm instead of 6,000 rpm.

Production Example 7

Magnetic silica particles (S7) were prepared in the same manner as in Production Example 5 except that the amount of the tetraethoxysilane was 0.5 parts instead of 2.2 parts.

Production Example 8

Magnetic silica particles (S8) were prepared in the same manner as in Production Example 7 except that the rotation rate of CLEARMIX in the emulsification was 7,500 rpm instead of 6,000 rpm.

Production Example 9

Magnetic silica particles (S9) were prepared in the same manner as in Production Example 2 except that the amount of the water mixed with the 25% ammonia water (3.8 parts) in the production of magnetite particles was 55 parts instead of 100 parts and the amount of the tetraethoxysilane was 1.2 parts instead of 2.2 parts.

Comparative Production Example 1

Magnetic silica particles (H1) were prepared in the same manner as in Production Example 4 except that the amount of the tetraethoxysilane was 8.0 parts instead of 0.5 parts.

Comparative Production Example 2

Magnetic silica particles (H2) were prepared in the same manner as in Production Example 9 except that the amount of the tetraethoxysilane was 12.5 parts instead of 1.2 parts.

Comparative Production Example 3

Magnetic silica particles (H3) were prepared in the same manner as in Production Example 9 except that the amount of the tetraethoxysilane was 8.0 parts instead of 1.2 parts and the rotation rate of CLEARMIX in the emulsification was 6,000 rpm instead of 7,500 rpm.

Comparative Production Example 4

Ferrous sulfate (100 parts) was dissolved in water (1,000 parts). A solution of sodium hydroxide (28.8 parts) in water (500 parts) was dropwise added thereto over one hour under stirring. The mixture was heated up to 85° C. under stirring, and air was bubbled into the suspension so that the suspension was oxidized for eight hours. The suspension was centrifuged to provide magnetite particles. The obtained magnetite particles (2.2 parts) were mixed with decane (5.7 parts) and tetraethoxysilane (2.2 parts), thereby providing a dispersion (R-1). Magnetic silica particles (H4) were prepared in the same manner as in Production Example 2 except that the dispersion (R-1) was used instead of the dispersion (A2-1).

Comparative Production Example 5

Magnetic silica particles (H5) were prepared in the same manner as in Comparative Production Example 4 except that the amount of the tetraethoxysilane was 12.5 parts instead of 2.2 parts.

Comparative Production Example 6

Magnetite particles (Sigma-Aldrich Japan) (2.2 parts) having an average particle size of 50 nm were mixed with decane (5.7 parts) and tetraethoxysilane (2.2 parts), providing a dispersion (R-2). Magnetic silica particles (H6) were prepared in the same manner as in Production Example 1 except that the dispersion (R-2) was used instead of the dispersion (A2-1).

Example 1

The following operations provided a magnetic silica particle-containing reagent (anti-AFP antibody-immobilized magnetic silica particle reagent), a labeled reagent (POD-labeled anti-AFP antibody reagent), and the reagent of the present invention including a first chemiluminescence reagent and a second chemiluminescence reagent.

Preparation of Magnetic Silica Particle-Containing Reagent:

A solution (40 mL) of 1% by weight γ-aminopropyltriethoxysilane in acetone was charged into a polyethylene bottle with a lid. The magnetic silica particles (S1) (40 mg) produced in Production Example 1 were added thereto, and the components were reacted at 25° C. for one hour. The magnetic silica particles were collected using a neodymium magnet, and the liquid was aspiration-removed using an aspirator. Deionized water (40 mL) was added into the bottle and the lid was put on the bottle, and then the polystyrene bottle was slowly inverted twice so that the components were stirred. The magnetic silica particles were collected using a neodymium magnet and the liquid was aspiration-removed using an aspirator, and subsequently the magnetic silica particles were washed. The washing operation was repeated three times. Next, the washed magnetic silica particles were charged into a polyethylene bottle with a lid containing a solution (40 mL) of 2% by weight glutaraldehyde in water, and the components were reacted at 25° C. for one hour. Deionized water (40 mL) was added thereto and the lid was put on the bottle, and then the polystyrene bottle was slowly inverted twice so that the components were stirred. The magnetic silica particles were collected using a neodymium magnet and the liquid was aspiration-removed using an aspirator, and subsequently the magnetic silica particles were washed. The washing operation was repeated three times. The washed magnetic silica particles were charged into a polyethylene bottle with a lid containing a 0.02 M phosphate buffer (pH: 8.7) (40 mL) that contains an anti-AFP monoclonal antibody (Dako Japan Inc.) at a concentration of 20 μg/mL, and the components were reacted at 25° C. for one hour. After the reaction, the magnetic silica particles were collected using a neodymium magnet and the anti-AFP antibody-containing phosphate buffer was removed, thereby providing anti-AFP antibody-immobilized magnetic silica particles. The particles were diluted in a 0.02 M phosphate buffer (pH: 7.0) containing 1% bovine serum albumin such that the concentration of the anti-AFP antibody-bound magnetic silica particles was 0.5 mg/mL to prepare a magnetic silica particle-containing reagent, and the reagent was put into cold storage (2° C. to 10° C.)

Preparation of Labeled Reagent:

With an anti-AFP polyclonal antibody (Dako Japan Inc.) and horseradish-derived POD (TOYOBO CO., LTD.), a POD-labeled anti-AFP antibody was prepared by the method disclosed in the document (S. YOSHITAKE, M. IMAGAWA, E. ISHIKAWA, et al., J. Biochem, Vol. 92, 1982, 1413-1424). This antibody was diluted in a 0.02 M phosphate buffer (pH: 7.0) containing a 1% bovine serum albumin such that the concentration of the POD-labeled anti-AFP antibody was 200 nM to prepare a labeled reagent, and the reagent was put into cold storage (2° C. to 10° C.)

Preparation of First Chemiluminescence Reagent:

A 1,000-mL volumetric flask was charged with luminol sodium salt (Sigma-Aldrich Japan) (0.7 g) and 4-(cyanomethylthio)phenol (0.1 g). A 3-[4-(2-hydroxyethyl)-1-piperazinyl]propanesulfonic acid/sodium hydroxide buffer (10 mM, pH: 8.6) was charged therein such that the volume of the solution reached 1,000 mL. The components were uniformly mixed at 25° C. to prepare a first chemiluminescence reagent. The reagent was put into cold storage (2° C. to 10° C.) until the measurement.

Preparation of Second Chemiluminescence Reagent:

A 1,000-mL volumetric flask was charged with hydrogen peroxide (Wako Pure Chemical Industries, Ltd., JIS Special Grade, concentration: 30% by weight) (6.6 g). Deionized water was charged therein such that the volume of the solution reached 1,000 mL. The components were uniformly mixed at 25° C. to prepare a second chemiluminescence reagent. The reagent was put into cold storage (2° C. to 10° C.) until the measurement.

Examples 2 to 9 and Comparative Examples 1 to 6

In each example, the magnetic silica particle-containing reagent of the present invention or a magnetic silica particle-containing reagent for comparison, a labeled reagent, and the reagent of the present invention including a first chemiluminescence reagent and a second chemiluminescence reagent were produced in the same manner as in Example 1 except that one type of the magnetic silica particles (S2) to (S9) and (H1) to (H6) was used instead of the magnetic silica particles (S1).

With the obtained reagents, short-time immunoassay was performed as follows. Table 1 shows the results of evaluating the washability and sensitivity. With respect to the magnetic silica particles (S1) to (S9) and (H1) to (H6) used herein, the average particle size of the superparamagnetic metal oxide, the average particle size of the magnetic silica particles, and the amount of the superparamagnetic metal oxide were measured as follows, evaluating the magnetic collectability, redispersibility, and reaggregability. Table 1 shows the results of these evaluations.

<Method of Evaluating Washability and Sensitivity in Short-Time Immunoassay Using the Reagents of the Present Invention>

The magnetic silica particle-containing reagent (0.025 mL) and a standard AFP solution (0.025 mL) at an AFP concentration of 2 ng/mL prepared using a phosphate buffer containing 1% by weight bovine serum albumin were mixed in a test tube, and they were reacted at 37° C. for three minutes in the test tube, thereby providing a complex of anti-AFP antibody-immobilized magnetic silica particles and AFP. After the reaction, the magnetic silica particles were collected using a neodymium magnet from the outside of the test tube for 10 seconds and the liquid in the test tube was removed using an aspirator. Then, the neodymium magnet was moved away from the side face of the test tube sufficiently, and a physiological saline solution (0.5 mL) was added so that the magnetic silica particles were dispersed. The magnetic silica particles were magnetically collected and the liquid was removed using an aspirator. This washing operation was repeated three times.

The labeled reagent (0.025 mL) was put into the test tube and reacted at 37° C. for three minutes in the test tube, thereby providing a complex of anti-AFP antibody-immobilized magnetic silica particles, AFP, and POD-labeled anti-AFP antibody. After the reaction, the magnetic silica particles were collected using a neodymium magnet from the outside of the test tube for 10 seconds and the liquid in the test tube was removed using an aspirator. Then, the neodymium magnet was moved away from the side face of the test tube sufficiently, and a physiological saline solution (0.5 mL) was added so that the magnetic silica particles were dispersed. The magnetic silica particles were magnetically collected and the liquid was removed using an aspirator. This washing operation was repeated twice.

Finally, the first chemiluminescence reagent (0.07 mL) and the second chemiluminescence reagent (0.07 mL) were added at the same time, leading to a luminescent reaction at 37° C. for 43 seconds. The average luminescence intensity was measured 43 to 45 seconds after the addition of the chemiluminescence reagents using a luminometer (Lumat LB9507, Berthold Japan co. ltd.). The same operation was performed using a standard AFP solution at an AFP concentration of 0 ng/mL instead of the standard AFP solution at an AFP concentration of 2 ng/mL. This was treated as background.

The washability was evaluated on the basis of the following criteria relating to the average luminescence intensity in the immunoassay using a standard solution at an AFP concentration of 0 ng/mL.

○: The average luminescence intensity was less than 10,000 cps.

Δ: The average luminescence intensity was 10,000 cps or more but less than 30,000 cps.

×: The average luminescence intensity was 30,000 cps or more.

The sensitivity was evaluated on the basis of the following criteria relating to the difference between the luminescence intensities in the immunoassays using standard solutions at AFP concentrations of 0 ng/mL and 2 ng/mL.

○: The difference was 25,000 cps or more.

Δ: The difference was 10,000 cps or more but less than 25,000 cps.

×: The difference was less than 10,000 cps.

<Method of Measuring Average Particle Size of Superparamagnetic Metal Oxide>

The particle sizes of any 200 particles of superparamagnetic metal oxide were measured using a scanning electron microscope, and the average value thereof was treated as the average particle size.

<Method of Measuring Average Particle Size of Magnetic Silica Particles>

The particle sizes of any 200 magnetic silica particles were measured using a scanning electron microscope, and the average value thereof was treated as the average particle size.

<Method of Measuring Amount of Superparamagnetic Metal Oxide in Magnetic Silica Particles>

Any 20 magnetic silica particles were observed using a scanning electron microscope and the amount of the superparamagnetic metal oxide in each particle was measured using an energy dispersive X-ray spectrometer. The average value thereof was treated as the amount.

<Method of Evaluating Magnetic Collectability of Magnetic Silica Particles>

The magnetic silica particles (1.0 mg) was dispersed in ion exchange water (2 mL), and the dispersion was charged into a glass container with a size of mouth inner diameter×bottle diameter×total height=φ10.3 mm×φ12.0 mm×35 mm. A neodymium magnet with a size of 1 cm×1 cm×1 cm was placed on the side face of the bottle, and the time until the initial absorbance reached 20% was measured. The absorbance was evaluated on the basis of the following criteria.

○: The time was shorter than 15 seconds.

Δ: The time was 15 seconds or longer but shorter than 30 seconds.

×: The time was 30 seconds or longer.

<Method of Evaluating Redispersibility of Magnetic Silica Particles>

The magnetic silica particles (1.0 mg) was dispersed in ion exchange water (2 mL), and the dispersion was charged into a glass container with a size of mouth inner diameter×bottle diameter×total height=φ10.3 mm×φ12.0 mm×35 mm. A neodymium magnet with a size of 1 cm×1 cm×1 cm was placed on the side face of the bottle. Then, the magnetic silica particles were magnetically collected completely, the supernatant was removed, and the neodymium magnet was moved sufficiently away from the side face. Ion exchange water (2 mL) was spray-added to the magnetic silica particles and they were mixed by three-time pipetting. Within 10 seconds after the mixing, the dispersion was microscopically observed and the proportion of the number of aggregated particles to the total number of particles in the observed field was calculated. The redispersibility was evaluated on the basis of the following criteria.

○: The proportion was lower than 5%.

Δ: The proportion was 5% or higher but lower than 20%.

×: The proportion was 20% or higher.

<Method of Evaluating Reaggregability of Magnetic Silica Particles>

The proportion of the number of aggregated particles to the total number of particles in the observed field was calculated in the same manner as in the evaluation of the redispersibility except that the time until microscopic observation after three-time pipetting was five minutes instead of within 10 seconds. The reaggregability was evaluated on the basis of the following criteria.

○: The proportion was lower than 5%.

Δ: The proportion was 5% or higher but lower than 20%.

×: The proportion was 20% or higher.

TABLE 1

| | Physical properties and performance of magnetic silica particles | | | | | | | |
|---|---|---|---|---|---|---|---|---|
| | Evaluation with reagent | | Type of magnetic silica particles | Superparamagnetic metal oxide | | Average particle size of magnetic silica particles (μm) | Magnetic collectability | Redispersibility | Reaggregability |
| | Washability | Immunoassay sensitivity | | Average particle size (nm) | Amount (%) | | | | |
| Example 1 | ○ | ○ | (S1) | 1.4 | 64 | 4.6 | ○ | ○ | ○ |
| Example 2 | ○ | ○ | (S2) | 1.4 | 67 | 1.3 | ○ | ○ | ○ |
| Example 3 | ○ | ○ | (S3) | 1.4 | 93 | 4.5 | ○ | ○ | ○ |
| Example 4 | ○ | ○ | (S4) | 1.4 | 94 | 1.2 | ○ | ○ | ○ |
| Example 5 | ○ | ○ | (S5) | 13.4 | 65 | 4.2 | ○ | ○ | ○ |
| Example 6 | ○ | ○ | (S6) | 13.4 | 64 | 1.5 | ○ | ○ | ○ |
| Example 7 | ○ | ○ | (S7) | 13.4 | 92 | 3.8 | ○ | ○ | ○ |
| Example 8 | ○ | ○ | (S8) | 13.4 | 93 | 1.4 | ○ | ○ | ○ |
| Example 9 | ○ | ○ | (S9) | 12.5 | 82 | 1.8 | ○ | ○ | ○ |
| Comparative Example 1 | ○ | × | (H1) | 1.4 | 43 | 2.6 | × | ○ | ○ |

TABLE 1-continued

Physical properties and performance of magnetic silica particles

| | Evaluation with reagent | | Type of magnetic silica particles | Superparamagnetic metal oxide | | Average particle size of magnetic silica particles (μm) | Magnetic collectability | Redispersibility | Reaggregability |
|---|---|---|---|---|---|---|---|---|---|
| | Washability | Immunoassay sensitivity | | Average particle size (nm) | Amount (%) | | | | |
| Comparative Example 2 | ○ | x | (H2) | 12.5 | 25 | 1.8 | x | ○ | ○ |
| Comparative Example 3 | Δ | Δ | (H3) | 12.5 | 46 | 4.3 | Δ | Δ | Δ |
| Comparative Example 4 | x | x | (H4) | 230 | 60 | 1.8 | ○ | x | x |
| Comparative Example 5 | x | x | (H5) | 230 | 25 | 4.2 | Δ | Δ | x |
| Comparative Example 6 | Δ | Δ | (H6) | 50 | 50 | 4.5 | ○ | Δ | x |

INDUSTRIAL APPLICABILITY

The method of assaying an analyte using magnetic silica particles of the present invention can assay the analyte easily in a short time at high sensitivity owing to the magnetic characteristics of the magnetic silica particles and the redispersibility of the particles after magnetic collection. Thus, the assay method can be applied to a wide variety of clinical testing such as radioimmunoassay, enzyme immunoassay, fluorescent immunoassay, and chemiluminescence immunoassay. The reagent of the present invention is suitable for the assay method, and can be used as reagents for clinical testing such as radioimmunoassay, enzyme immunoassay, fluorescent immunoassay, and chemiluminescence immunoassay.

The invention claimed is:

1. A method of assaying an analyte in a sample in which magnetic silica particles are used,
    wherein the magnetic silica particles comprise silica particles containing 60 to 95% by weight of a superparamagnetic metal oxide that has an average particle size of 1 to 15 nm; and an analyte-binding substance that is a substance capable of specifically binding to the analyte and is immobilized on a surface of the silica particles, and
    wherein the method comprises:
    bringing a sample containing the analyte, the magnetic silica particles, and a labeled analyte-binding substance that is an analyte-binding substance labeled by a label into contact with each other to form a labeled complex that is a complex of the analyte-binding substance, the analyte, and the labeled analyte-binding substance on the magnetic silica particles;
    B/F-separating the magnetic silica particles carrying the labeled complex;
    measuring the amount of the label in the labeled complex; and
    assaying the analyte in the sample based on the resulting amount of the label.

2. A method of assaying an analyte in a sample in which magnetic silica particles are used,
    wherein the magnetic silica particles comprise silica particles containing 60 to 95% by weight of a superparamagnetic metal oxide that has an average particle size of 1 to 15 nm; and the analyte or an analog of the analyte immobilized on a surface of the silica particles, and
    wherein the method comprises:
    bringing a sample containing the analyte, a labeled analyte-binding substance that is a substance labeled by a label and is capable of specifically binding to the analyte, and the magnetic silica particles into contact with each other to form a labeled complex that is a complex of the analyte or the analog of the analyte and the labeled analyte-binding substance on the magnetic silica particles;
    B/F-separating the magnetic silica particles carrying the labeled complex;
    measuring the amount of the label in the labeled complex; and
    assaying the analyte in the sample based on the resulting amount of the label.

3. A method of assaying an analyte in a sample in which magnetic silica particles are used,
    wherein the magnetic silica particles comprise silica particles containing 60 to 95% by weight of a superparamagnetic metal oxide that has an average particle size of 1 to 15 nm; and an analyte-binding substance that is a substance capable of specifically binding to the analyte immobilized on a surface of the silica particles, and
    wherein the method comprises:
    bringing a sample containing the analyte, a labeled analyte or analog thereof that is an analyte or analog of the analyte labeled by a label, and the magnetic silica particles into contact with each other to form a labeled complex that is a complex of the analyte-binding substance and the labeled analyte or analog on the magnetic silica particles;
    B/F-separating the magnetic silica particles carrying the labeled complex;
    measuring the amount of the label in the labeled complex; and
    assaying the analyte in the sample based on the resulting amount of the label.

4. The assay method according to claim 1, wherein the B/F separation is performed utilizing the magnetism of the magnetic silica particles.

5. The assay method according to claim 1, wherein the magnetic silica particles have an average particle size of 1 to 5 μm.

6. The assay method according to claim 1, wherein the superparamagnetic metal oxide is an iron oxide.

7. The assay method according to claim 6,
wherein the iron oxide is at least one selected from the group consisting of magnetite, γ-hematite, an intermediate iron oxide between magnetite and α-hematite, and an intermediate iron oxide between γ-hematite and α-hematite.

8. The assay method according to claim 1,
wherein at least one organic compound selected from the group consisting of glutaraldehyde, albumin, carbodiimide, streptavidin, biotin, and functional group-containing alkylalkoxysilanes is bound to the surface of the magnetic silica particles before the immobilization of the substance capable of specifically binding to the analyte on the surface of the magnetic silica particles.

9. The assay method according to claim 8,
wherein the functional group of the alkylalkoxysilanes is at least one selected from the group consisting of an amino group, a carboxyl group, a hydroxy group, a mercapto group, and a glycidyloxy group.

10. The assay method according to claim 1,
wherein the substance capable of specifically binding to the analyte is an antibody against the analyte or an analog of the analyte, an antigen capable of binding to the analyte or the analog of the analyte, or a protein capable of binding to the analyte or the analog of the analyte.

11. A reagent for the assay method according to claim 1, comprising
magnetic silica particles comprising:
silica particles containing 60 to 95% by weight of a superparamagnetic metal oxide that has an average particle size of 1 to 15 nm; and
a substance capable of specifically binding to an analyte immobilized on a surface of the silica particles.

12. The reagent according to claim 11,
wherein the magnetic silica particles have an average particle size of 1 to 5 μm.

13. The reagent according to claim 11,
wherein the superparamagnetic metal oxide is an iron oxide.

14. The reagent according to claim 13,
wherein the iron oxide is at least one selected from the group consisting of magnetite, γ-hematite, an intermediate iron oxide between magnetite and α-hematite, and an intermediate iron oxide between γ-hematite and α-hematite.

15. The reagent according to claim 11,
wherein at least one organic compound selected from the group consisting of glutaraldehyde, albumin, carbodiimide, streptavidin, biotin, and functional group-containing alkylalkoxysilanes is bound to the surface of the magnetic silica particles before the immobilization of the substance capable of specifically binding to the analyte on the surface of the magnetic silica particles.

16. The reagent according to claim 15,
wherein the functional group of the alkylalkoxysilanes is at least one selected from the group consisting of an amino group, a carboxyl group, a hydroxy group, a mercapto group, and a glycidyloxy group.

17. The reagent according to claim 11,
wherein the substance capable of specifically binding to the analyte is an antibody against the analyte or an analog of the analyte, an antigen capable of binding to the analyte or the analog of the analyte, or a protein capable of binding to the analyte or the analog of the analyte.

18. The assay method according to claim 2,
wherein the B/F separation is performed utilizing the magnetism of the magnetic silica particles.

19. The assay method according to claim 2,
wherein the magnetic silica particles have an average particle size of 1 to 5 μm.

20. The assay method according to claim 2,
wherein the superparamagnetic metal oxide is an iron oxide.

21. The assay method according to claim 20,
wherein the iron oxide is at least one selected from the group consisting of magnetite, γ-hematite, an intermediate iron oxide between magnetite and α-hematite, and an intermediate iron oxide between γ-hematite and α-hematite.

22. The assay method according to claim 2,
wherein at least one organic compound selected from the group consisting of glutaraldehyde, albumin, carbodiimide, streptavidin, biotin, and functional group-containing alkylalkoxysilanes is bound to the surface of the magnetic silica particles before the immobilization of the analyte or the analog of the analyte on the surface of the magnetic silica particles.

23. The assay method according to claim 22,
wherein the functional group of the alkylalkoxysilanes is at least one selected from the group consisting of an amino group, a carboxyl group, a hydroxy group, a mercapto group, and a glycidyloxy group.

24. The assay method according to claim 2,
wherein the labeled analyte-binding substance is an antibody against the analyte or the analog of the analyte, an antigen capable of binding to the analyte or the analog of the analyte, or a protein capable of binding to the analyte or the analog of the analyte.

25. A reagent for the assay method according to claim 2, comprising
magnetic silica particles comprising:
silica particles containing 60 to 95% by weight of a superparamagnetic metal oxide that has an average particle size of 1 to 15 nm; and
an analyte or an analog of the analyte immobilized on a surface of the silica particles.

26. The reagent according to claim 25,
wherein the magnetic silica particles have an average particle size of 1 to 5 μm.

27. The reagent according to claim 25,
wherein the superparamagnetic metal oxide is an iron oxide.

28. The reagent according to claim 27,
wherein the iron oxide is at least one selected from the group consisting of magnetite, γ-hematite, an intermediate iron oxide between magnetite and α-hematite, and an intermediate iron oxide between γ-hematite and α-hematite.

29. The reagent according to claim 25,
wherein at least one organic compound selected from the group consisting of glutaraldehyde, albumin, carbodiimide, streptavidin, biotin, and functional group-containing alkylalkoxysilanes is bound to the surface of the magnetic silica particles before the immobilization of the analyte or the analog of the analyte on the surface of the magnetic silica particles.

30. The reagent according to claim 29,
wherein the functional group of the alkylalkoxysilanes is at least one selected from the group consisting of an amino group, a carboxyl group, a hydroxy group, a mercapto group, and a glycidyloxy group.

31. The reagent according to claim 25,
comprising a labeled analyte-binding substance that is a substance labeled by a label and is capable of specifically binding to the analyte, wherein the labeled analyte-binding substance is an antibody against the analyte or the analog of the analyte, an antigen capable of binding to the analyte or the analog of the analyte, or a protein capable of binding to the analyte or the analog of the analyte.

32. The assay method according to claim 3, wherein the B/F separation is performed utilizing the magnetism of the magnetic silica particles.

33. The assay method according to claim 3, wherein the magnetic silica particles have an average particle size of 1 to 5 μm.

34. The assay method according to claim 3, wherein the superparamagnetic metal oxide is an iron oxide.

35. The assay method according to claim 34, wherein the iron oxide is at least one selected from the group consisting of magnetite, γ-hematite, an intermediate iron oxide between magnetite and α-hematite, and an intermediate iron oxide between γ-hematite and α-hematite.

36. The assay method according to claim 3, wherein at least one organic compound selected from the group consisting of glutaraldehyde, albumin, carbodiimide, streptavidin, biotin, and functional group-containing alkylalkoxysilanes is bound to the surface of the magnetic silica particles before the immobilization of the substance capable of specifically binding to the analyte on the surface of the magnetic silica particles.

37. The assay method according to claim 36, wherein the functional group of the alkylalkoxysilanes is at least one selected from the group consisting of an amino group, a carboxyl group, a hydroxy group, a mercapto group, and a glycidyloxy group.

38. The assay method according to claim 3, wherein the substance capable of specifically binding to the analyte is an antibody against the analyte or an analog of the analyte, an antigen capable of binding to the analyte or the analog of the analyte, or a protein capable of binding to the analyte or the analog of the analyte.

39. A reagent for the assay method according to claim 3, comprising
magnetic silica particles comprising:
silica particles containing 60 to 95% by weight of a superparamagnetic metal oxide that has an average particle size of 1 to 15 nm; and
a substance capable of specifically binding to an analyte immobilized on a surface of the silica particles.

40. The reagent according to claim 39, wherein the magnetic silica particles have an average particle size of 1 to 5 μm.

41. The reagent according to claim 39, wherein the superparamagnetic metal oxide is an iron oxide.

42. The reagent according to claim 41, wherein the iron oxide is at least one selected from the group consisting of magnetite, γ-hematite, an intermediate iron oxide between magnetite and α-hematite, and an intermediate iron oxide between γ-hematite and α-hematite.

43. The reagent according to claim 39, wherein at least one organic compound selected from the group consisting of glutaraldehyde, albumin, carbodiimide, streptavidin, biotin, and functional group-containing alkylalkoxysilanes is bound to the surface of the magnetic silica particles before the immobilization of the substance capable of specifically binding to the analyte on the surface of the magnetic silica particles.

44. The reagent according to claim 43, wherein the functional group of the alkylalkoxysilanes is at least one selected from the group consisting of an amino group, a carboxyl group, a hydroxy group, a mercapto group, and a glycidyloxy group.

45. The reagent according to claim 39, wherein the substance capable of specifically binding to the analyte is an antibody against the analyte or an analog of the analyte, an antigen capable of binding to the analyte or the analog of the analyte, or a protein capable of binding to the analyte or the analog of the analyte.

* * * * *